(12) United States Patent
Ma et al.

(10) Patent No.: US 10,357,528 B2
(45) Date of Patent: Jul. 23, 2019

(54) COMPOSITION FOR TREATING CORNEAL DISEASES OR CONJUNCTIVAL DISEASES

(71) Applicant: KOREA INSTITUTE OF ORIENTAL MEDICINE, Daejeon (KR)

(72) Inventors: Jin Yeul Ma, Daejeon (KR); Jung Hyun Kim, Daejeon (KR); Jong Wook Jeon, Daejeon (KR); You Chang Oh, Daejeon (KR); Won Kyung Cho, Daegu (KR); Youn Hwan Hwang, Daejeon (KR); Nam Hui Yim, Daejeon (KR); Jae Myung Yoo, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 15/742,391

(22) PCT Filed: Jul. 8, 2016

(86) PCT No.: PCT/KR2016/007416
§ 371 (c)(1),
(2) Date: May 21, 2018

(87) PCT Pub. No.: WO2017/007273
PCT Pub. Date: Jan. 12, 2017

(65) Prior Publication Data
US 2018/0264064 A1 Sep. 20, 2018

(30) Foreign Application Priority Data
Jul. 8, 2015 (KR) .................. 10-2015-0097387

(51) Int. Cl.
| | | |
|---|---|---|
| *A61P 27/02* | (2006.01) | |
| *A61K 36/20* | (2006.01) | |
| *A61K 9/08* | (2006.01) | |
| *A61K 36/77* | (2006.01) | |
| *A61K 9/00* | (2006.01) | |
| *A61K 47/02* | (2006.01) | |

(52) U.S. Cl.
CPC ............ *A61K 36/77* (2013.01); *A61K 9/0048* (2013.01); *A61K 9/08* (2013.01); *A61K 36/20* (2013.01); *A61K 47/02* (2013.01); *A61P 27/02* (2018.01)

(58) Field of Classification Search
CPC .......... A61K 36/20; A61K 36/77; A61K 8/97; A61K 9/00; A61K 9/0048; A61P 27/02
See application file for complete search history.

(56) References Cited

FOREIGN PATENT DOCUMENTS

| | | |
|---|---|---|
| KR | 10-2010-0004466 | 1/2010 |
| KR | 10-1089779 B1 | 12/2011 |
| KR | 10-1326162 B1 | 11/2013 |
| KR | 10-1484948 B1 | 1/2015 |
| WO | WO 95-22254 A1 | 8/1995 |

OTHER PUBLICATIONS

Bi, Wu, et al J. "Traditional Uses, Phytochemistry, and Pharmacology of the Genus *Acer* (Maple): A Review" Ethnophamacology, 189, Apr. 29, 2016, pp. 31-60; http://dx.doi.org/10.1016/j.jep.2016.04.021. (Year: 2016).*

Oh, Tae woo, et al "Leaves of *Acer palmatum* thumb. Rescues N-ethyl-N-nitrosourea (ENU)-Induced Retinal Degeneration in Mice" Phytomedicine, 42, Mar. 15, 2018, pp. 51-55; doi: 10.1016/j.phymed.2018.03.026. (Year: 2018).*

Ogundele et al, "In vivo comparative study of ocular vasodilation, a relative indicator of hyperemia, in guinea pigs following treatment with bimatoprost ophthalmic solutions 0.01% and 0.03%." *Clinical ophthalmology* (Auckland, NZ) 4 (2010): 649.

* cited by examiner

*Primary Examiner* — Aaron J Kosar
(74) *Attorney, Agent, or Firm* — Parker Highlander PLLC

(57) ABSTRACT

The present invention relates to a pharmaceutical composition for preventing and treating corneal diseases or conjunctival diseases, containing a maple leaf extract as an active ingredient. The maple leaf extract exhibits an effect of inhibiting hyperemia in the eyeball in which hyperemia has been induced and an effect of inhibiting angiogenesis in the eyeball in which corneal damage has been induced, thus being effectively used in a pharmaceutical composition for preventing and treating corneal diseases or conjunctival diseases.

7 Claims, 4 Drawing Sheets

| | Before inducing hyperemia | After inducing hyperemia | | Before inducing hyperemia | After inducing hyperemia |
|---|---|---|---|---|---|
| Group induced with hyperemia |  |  | | | |
| Group with low EE concentration |  |  | Group with low EW concentration |  |  |
| Group with medium EE concentration |  |  | Group with medium EW concentration |  |  |
| Group with high EE concentration |  |  | Group with high EW concentration |  |  |

COMPOSITION FOR TREATING CORNEAL DISEASES OR CONJUNCTIVAL DISEASES

This application is a national phase application under 35 U.S.C. § 371 of International Application No. PCT/KR2016/007416, filed Jul. 8, 2016, which claims priority to Korean Application No. 10-2015-0097387, filed Jul. 8, 2015. The entire text of each of the above referenced disclosures is specifically incorporated herein by reference.

TECHNICAL FIELD

The present invention relates to a pharmaceutical composition for preventing or treating corneal diseases or conjunctival diseases containing a maple leaf extract. Additionally, the present invention relates to a method for preventing or treating corneal diseases or conjunctival diseases, which includes administering a pharmaceutical composition containing a maple leaf extract to the eyeball of a subject. Furthermore, the present invention relates to a cosmetic composition for preventing or ameliorating hyperemia containing a maple leaf extract.

BACKGROUND ART

Corneal diseases refer to all kinds of diseases that cause damage in transparent vision due to damage to the cornea, which has the role of protecting the eyeballs and the role of delivery by refracting the rays coming into the eyes to reach the retina. According to the Korea Research Foundation's classification of the field of ophthalmology, ophthalmic diseases are included in 8 subcategories of ophthalmology, and corneal diseases are included as one of the major fields of ophthalmic diseases.

Meanwhile, since the advent of personal computers in the 1980s, continuous use of the eye is becoming compulsory in the information society, where the spread of portable video devices including computers and the popularization of smart phones are common, regardless of gender and age, and thus the need for eye healthcare has become more important. Particularly, in recent years, symptoms of dry eye syndrome, which is known to be common in elderly people, have tended to increase even in young adults. Recently, as a side effect due to the increased use of contact lenses, the number of patients suffering from corneal angiogenic disease is on the rise. As a result of an investigation carried out in the Ulsan area with respect to patients with eye diseases in each age group, it was confirmed that the most common eye disease occurring in the 10 to 20 age group was keratitis, and that in the 30 to 50 age group was conjunctivitis, thus suggesting that among various eye diseases, corneal diseases account for the majority of eye diseases.

As a method for treating eye diseases, various treatment methods such as injection of drugs or laser treatment may be provided. Specifically, there is a therapeutic method of injecting a steroidal drug into the vitreous body as a method for treating corneal angiogenic disease, which is a kind of corneal disease. However, in this case, side effects such as hemorrhage, retinal detachment, etc. may occur due to injection of steroid drugs, and side effects such as the rise of intraocular pressure by drugs or cataract due to repeated injections may also appear.

In this regard, Korean Patent No. 132731 discloses the therapeutic effects of alcaftadine for treating ocular allergy and ocular redness. However, there is still a need for safer and more effective treatments.

DISCLOSURE

Technical Problem

A main object of the present invention is to provide a pharmaceutical composition for preventing or treating corneal diseases or conjunctival diseases containing a maple leaf extract.

Another object of the present invention is to provide a method for preventing or treating corneal diseases or conjunctival diseases including administering a pharmaceutical composition containing a maple leaf extract to the eyeball of a subject.

Still another object of the present invention is to provide a cosmetic composition for preventing or ameliorating hyperemia containing a maple leaf extract.

Technical Solution

The present inventors have made efforts to develop a composition containing a natural extract which has an effect of preventing or treating corneal diseases, such as hyperemia and corneal angiogenesis, without any side effects. As a result, they have confirmed that a maple leaf extract has inhibitory effects against hyperemia and corneal angiogenesis, thereby completing the present invention.

Advantageous Effects of the Invention

The maple leaf extract according to the present invention is effective for the prevention or treatment of corneal diseases or conjunctival diseases.

BEST MODE

Figure 1:
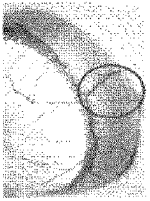
FIG. 1 shows images illustrating the degree of hyperemia before and after induction of hyperemia by capsaicin after administering a maple leaf extract to the eyeball of each rat.
Figure 1:
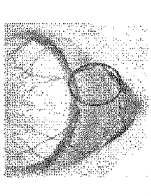
Figure 1:
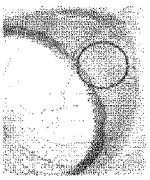
Figure 1:
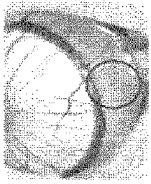
Figure 1:
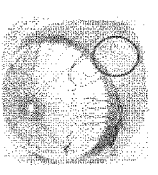
Figure 1:
Figure 1:
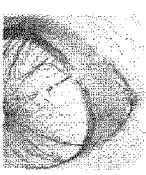
Figure 1:
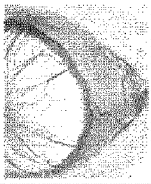
Figure 1:
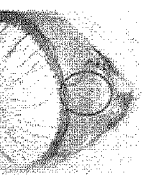
Figure 1:
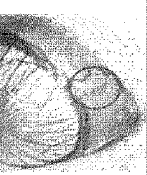
Figure 1:
Figure 1:
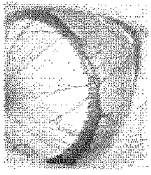
Figure 1:
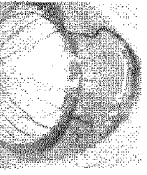
Figure 1:

To achieve the objects of the present invention, an aspect of the present invention provides a pharmaceutical composition for preventing or treating corneal diseases or conjunctival diseases containing a maple leaf extract.

As used herein, the term "maple (*Acer palmatum*)" refers to a plant, being a deciduous broad-leaved arboreous tree, which has a round shape and a height of about 10 m to 20 m.

As used herein, the term "extract" may refer to a resulting product, such as a liquid component which is obtained by immersing a desired material in various solvents followed by extracting at room temperature or in a heated state for a predetermined time, a solid component which is obtained by removing the solvent from the liquid component, etc. Furthermore, the extract may comprehensively be interpreted to include all of a diluted solution of the resulting products, a concentrated solution thereof, a crude product thereof, a purified product thereof, etc., in addition to the above resulting products.

Examples of the method to be used for obtaining the extract may preferably include a cold precipitation method in which roots, stems, leaves, fruits, flowers, dried products thereof, processed products, etc. of the maple (*Acer palmatum*) are immersed in any of the above solvents followed by extraction at room temperature of 10° C. to 25° C.; a heat extraction performed by applying heat at 40° C. to 100° C.; an ultrasonic extraction performed by applying ultrasonic waves; a reflux extraction performed using a reflux condenser, etc., but the method is not particularly limited thereto as long as the method can obtain an extract having an effect for preventing or treating corneal diseases or conjunctival diseases. In an embodiment, each of the extracts may be contained in an amount of 0.01 wt % to 100 wt %, and more preferably 1 wt % to 80 wt %, relative to the total weight of a pharmaceutical composition.

For example, the maple leaf extract may be an ethanol extract of maple leaves.

In an exemplary embodiment of the present invention, the extraction was performed by adding a pulverized product of maple leaves (1,700 g) into 25% ethanol (17 L) followed by sedimentation at room temperature. Then, the extract was concentrated under reduced pressure and lyophilized, and thereby a 25% ethanol extract of maple leaves was prepared.

In the present invention, the maple leaf extract may be a hot-water extract of maple leaves.

In an exemplary embodiment of the present invention, the extraction was performed by adding a pulverized product of maple leaves (1,700 g) into water (17 L) followed by sedimentation for 1 hour, subjected to hot-water extraction using the Gyeongseo Extractor (COSMOS 660, Incheon, Korea) for 3 hours, lyophilized, and thereby a hot-water extract of maple leaves was prepared.

In the present invention, the maple leaf extract may be prepared as a fraction thereof for use.

As used herein, the term "fraction" refers to a resulting product obtained by performing fractionation to separate a particular component or group of specific components from a mixture containing various components.

In the present invention, the fractionation method for obtaining a fraction is not particularly limited and may be performed according to a method commonly used in the art. A solvent fractionation method performed by treating various solvents, an ultrafiltration fractionation method performed by passing through an ultrafiltration membrane having a constant molecular weight cut-off value, a chromatography fractionation method performing various forms of chromatography (manufactured for separation according to size, charge, hydrophobicity, or affinity), a combination thereof, etc. In the present invention, the kind of the solvent used to obtain the fraction is not particularly limited, and any solvent known in the art can be used. Non-limiting examples of the fraction solvents may include water, an organic solvent, or a mixed solvent thereof. The organic solvent may be an alcohol having 1 to 4 carbon atoms, a polar solvent such as ethyl acetate, acetone, etc., a nonpolar solvent such as hexane and dichloromethane, or a mixed solvent thereof. Additionally, preferably, water, an alcohol having 1 to 4 carbon atoms, or a mixed solvent thereof, and more preferably, ethanol may be used. Each of the fractions may be contained in an amount of 0.001 wt % to 100 wt %, and more preferably 0.1 wt % to 80 wt %, relative to the total weight of a pharmaceutical composition.

As used herein, the term "cornea" refers to a transparent membrane on the surface of the eyeball in the middle region of the eye, which has a structure enabling the protection of the eye from the outside and allowing the light to pass through and refract, thereby allowing visual acuity.

As used herein, the term "corneal disease" refers to all of the diseases or damage that cause damage to the cornea, thereby causing a loss of transparent vision. Specifically, the corneal disease may be any one selected from the group consisting of dry eye syndrome, hyperemia, corneal angiogenesis, and keratitis, but the corneal disease is not limited thereto and any disease that may accompany hyperemia or may occur due to the corneal angiogenesis may be included without limitation.

Figure 2:
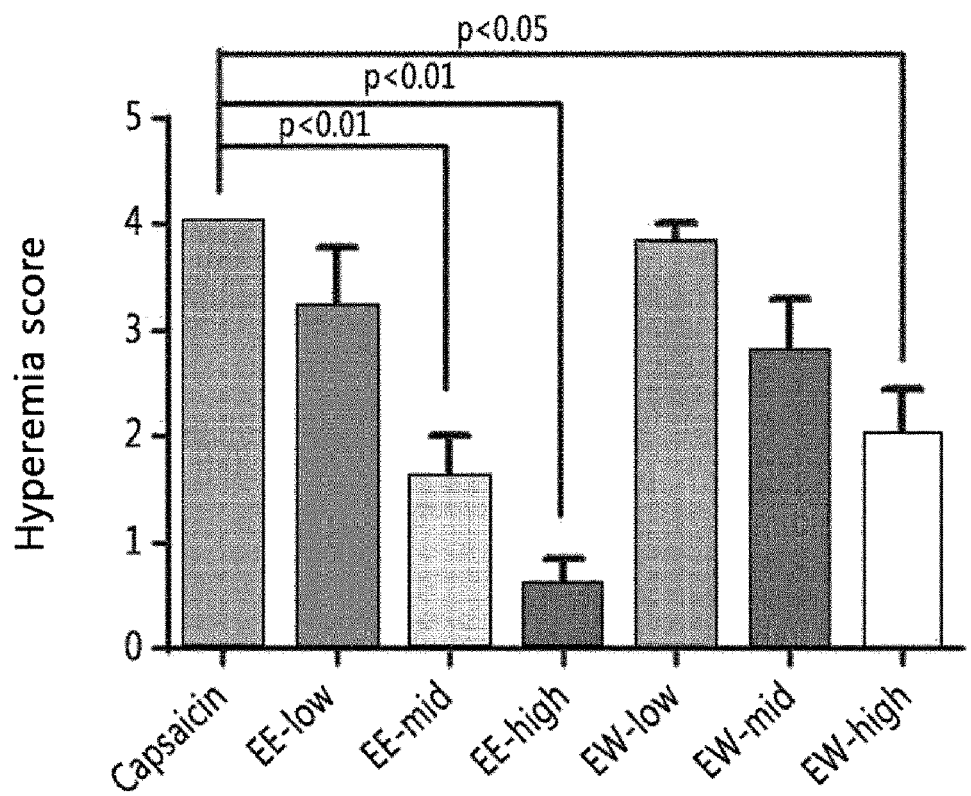
FIG. 2 shows a graph illustrating the degree of hyperemia represented in score in mice, where hyperemia was induced by capsaicin, after administering a maple leaf extract to the eyeball of each rat.

In an exemplary embodiment of the present invention, to confirm the inhibitory effect of a maple leaf extract against hyperemia, the degree of hyperemia was examined after administering a maple leaf extract into the eyeball of a rat followed by the administration with 1% capsaicin. As a result, it was confirmed that hyperemia was inhibited in a dose-dependent manner with respect to the maple leaf extract, and thus the maple leaf extract can be used for the therapeutic use of corneal diseases which have hyperemia as the main symptom (FIGS. 1 and 2).

Figure 3:
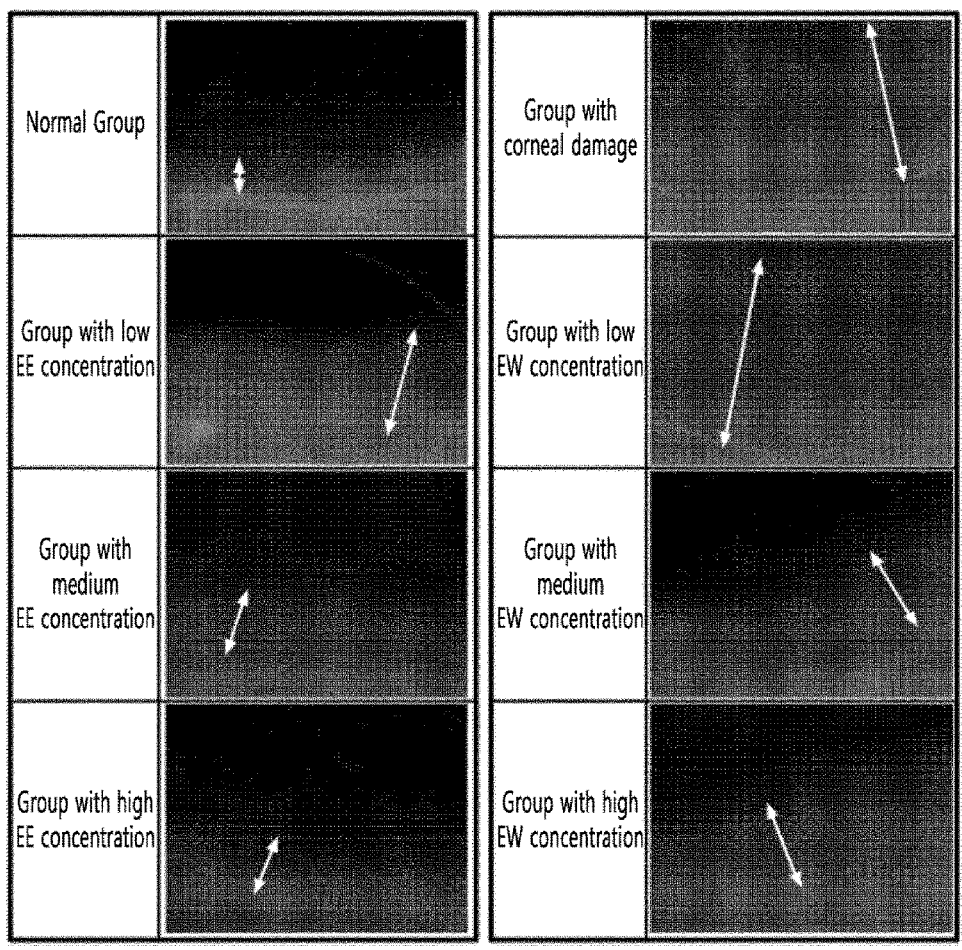
FIG. 3 shows images illustrating the degree of corneal angiogenesis after administering a maple leaf extract to the eyeball of each rat, where corneal damage was induced by sodium hydroxide.
Figure 4:
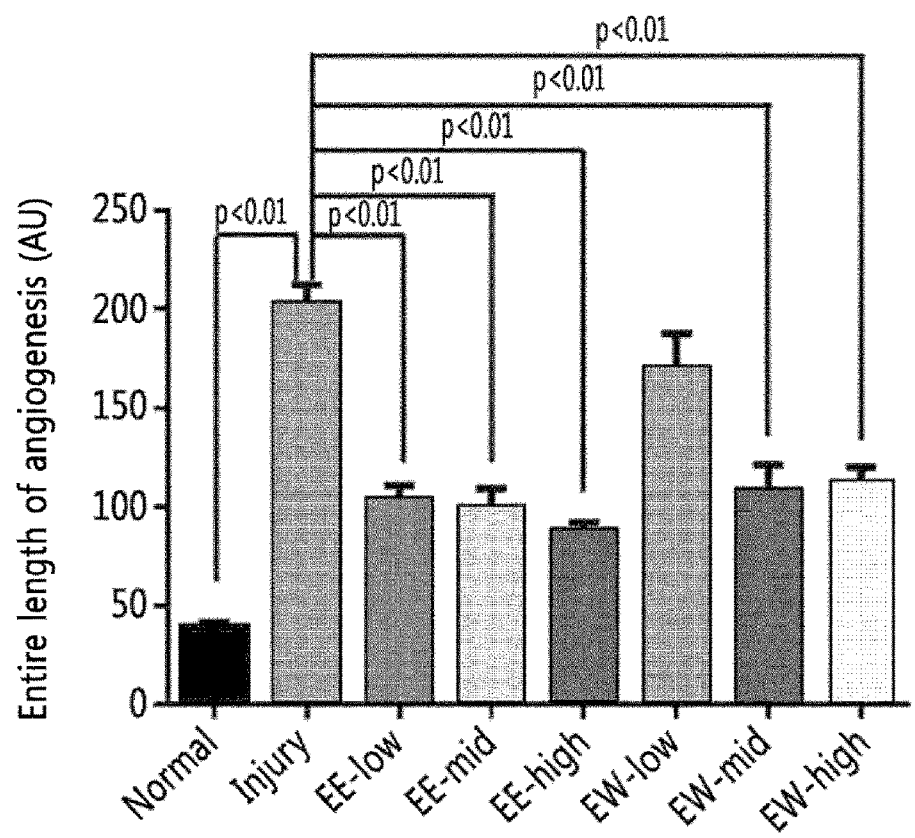
FIG. 4 shows images illustrating the length of corneal angiogenesis after administering a maple leaf extract to the eyeball of each rat, where corneal damage was induced by sodium hydroxide.

Additionally, in an exemplary embodiment of the present invention, to confirm the inhibitory effect of a maple leaf extract against corneal angiogenesis, the maple leaf extract was administered to a rat in which corneal damage was induced by an alkali burn. As a result, it was confirmed that corneal angiogenesis was inhibited in a dose-dependent manner with respect to the maple leaf extract, and thus the maple leaf extract can be used for the therapeutic use of corneal angiogenic disease (FIGS. 3 and 4).

As used herein, the term "dry eye syndrome" refers to an eye disease in which the tear is insufficient or excessively evaporated, or the tear components are not balanced, and thereby the eye surface is damaged, making the person feel symptoms of irritation such as irritability, foreign body sensation, and dry feeling.

As used herein, the term "hyperemia" refers to a pathological symptom in which blood vessels appear in the eyeballs, thus taking on a red color, and the blood vessels represent capillaries.

As used herein, the term "corneal angiogenesis" refers to a disease in which abnormal blood vessels are formed and enlarged in the transparent cornea where no blood vessels must be present, thus causing a loss of vision and eye damage.

As used herein, the term "keratitis" refers to a disease that causes inflammation in the cornea, resulting in pain, decreased vision, corneal opacity, etc., and the representative symptom, hyperemia, may occur.

As used herein, the term "conjunctiva" refers to a tissue that forms the surface of the eye together with the cornea, which protects the eye from external materials and is involved in the formation of the mucous layer of the tears and the immune function. As used herein, the term "conjunctival disease" refers to all of the diseases or impairments caused by damage to the conjunctiva, and specifically, it may be any one selected from the group consisting of conjunctivitis, pingueculitis, and pterygium, but the conjunctival disease is not limited thereto and may include without limitation any diseases that may be accompanied by hyperemia or arising from angiogenesis.

As used herein, the term "conjunctivitis" refers to an inflammatory disease which occurs in the conjunctiva that surrounds the eye from the outside, and it can be divided into infectious conjunctivitis and non-infectious conjunctivitis depending on the pathogenic cause. In the case of infectious conjunctivitis, it is caused by infection of various pathogens such as bacteria, viruses, fungi, etc., and in the case of non-infectious conjunctivitis, it is caused by an allergic reaction to foreign materials. Additionally, types of infectious conjunctivitis include epidemic conjunctivitis, acute hemorrhagic conjunctivitis (Apollo conjunctivitis), and bacterial conjunctivitis.

As used herein, the term "epidemic conjunctivitis" refers to conjunctivitis caused by adenovirus mostly in summer, which is highly contagious for 2 weeks after its onset.

As used herein, the term "acute hemorrhagic conjunctivitis", which is also called Apollo conjunctivitis, is conjunctivitis caused by enterovirus and is accompanied by a symptom of conjunctival hemorrhage.

As used herein, the term "bacterial conjunctivitis" is a conjunctivitis mainly caused by bacteria, and the causative pathogen may include *Streptococcus pneumoniae, Staphylococcus aureus, Neisseria gonorrhoeaem*, etc., but the causative pathogen is not limited thereto.

As used herein, the term "pingueculum" refers to a yellow node with a slightly protruding appearance on the inner conjunctiva near the cornea, and when inflammation occurs therein, it is called pingueculitis, and hyperemia may occur as its symptom.

As used herein, the term "pterygium" refers to a disease in which a fibrous tissue rich in blood vessels grows in a triangular shape, starting from the inner conjunctiva of the eye toward the center of the cornea beyond the boundary between the conjunctiva and the cornea.

As used herein, the term "prevention" refers to all kinds of actions associated with the inhibition or delay of corneal diseases or conjunctival diseases by administering a maple leaf extract according to the present invention to a subject.

As used herein, the term "treatment" refers to all kinds of actions associated with the improvement or advantageous changes in symptoms of corneal diseases or conjunctival diseases by administering the composition of the present invention to a subject suspected of having the above diseases.

As used herein, the term "subject" may refer to all of the animals, including humans, who currently have or are at risk of having corneal diseases or conjunctival diseases. The animal may be mammals including cattle, horses, sheep, pigs, goats, camel, antelopes, dogs, cats, etc. as well as humans in need of symptoms similar to those of corneal diseases or conjunctival diseases, but the animal is not limited thereto.

As used herein, the term "pharmaceutical composition" refers to one which was prepared for the purpose of preventing or treating diseases, and it may be formulated into various forms according to conventional methods and used. For example, the pharmaceutical composition may be formulated into powders, granules, tablets, capsules, suspensions, emulsions, syrups, etc. for oral preparations, or may be formulated in the form of external preparations and sterile injection solutions and used.

For example, the pharmaceutical composition may be an external preparation for the eyeball, and specifically, the pharmaceutical composition may be formulated into any one selected from the group consisting of eye ointments, eye drops, and sprays, but the pharmaceutical composition is not limited thereto and any formulation type used in the art for the administration into the eyeball may be used.

In the present invention, a pharmaceutical composition containing a maple leaf extract may further contain a pharmaceutically acceptable carrier.

As used herein, the term "pharmaceutically acceptable carrier" may refer to a carrier or diluent that does not inhibit the biological activity and characteristics of the compound being injected, without irritating the subject organism. The carrier type to be used in the present invention is not particularly limited but any carrier which is conventionally used in the art and pharmaceutically acceptable may be used. Non-limiting examples of the carrier may include saline, sterile water, Ringer's solution, buffered saline, albumin injection solution, dextrose solution, maltodextrin solution, glycerol, ethanol, etc. These carriers may be used alone or in a combination of two or more kinds. The carrier may contain a non-naturally occurring carrier. Additionally, if necessary, other conventional additives such as antioxidants, buffers, and/or bacteriostats may be added thereto, and a diluent, dispersant, surfactant, binder, lubricant, etc. may be further added and formulated into injectable preparations such as aqueous solutions, suspensions, emulsions, pills, capsules, granules, or tablets, etc.

Additionally, the pharmaceutical composition of the present invention may contain a pharmaceutically effective amount of a maple leaf extract. As used herein, the term "pharmaceutically effective amount" refers to an amount sufficient for the treatment of diseases at a reasonable benefit/risk ratio applicable to a medical treatment. Generally, the pharmaceutical composition may be administered once daily or in a few divided doses per day in an amount of 0.001 mg/kg to 1,000 mg/kg, preferably from 0.05 mg/kg to 200 mg/kg, and more preferably 0.1 mg/kg to 100 mg/kg. However, for the purpose of the present invention, the specific therapeutically effective amount of the composition for any particular patient is preferably applied differently depending on various factors including the kind and degree of response to be achieved, specific compositions including whether other agents are occasionally used therewith, the patient's age, weight, health conditions, sex and diet, administration time, administration route, excretion rate of the composition, duration of treatment, other drugs used in combination or simultaneously with the specific composition, and similar factors well known in the medical field.

The composition of the present invention may be administered as an individual therapeutic agent, in combination with other therapeutic agents, or sequentially or simultaneously with a conventional therapeutic agent(s), and may be administered once or multiple times. It is important to administer an amount to obtain the maximum effect with a minimum amount without adverse effects considering the factors described above, and these factors can easily be determined by one of ordinary skill in the art.

As used herein, the term "administration" refers to an introduction of the pharmaceutical composition of the present invention to a patient by any appropriate manner, and the maple leaf extract of the present invention may be administered through the eyeball as long as the extract is effective in the prevention or treatment of corneal diseases or conjunctival diseases.

Another aspect of the present invention provides a cosmetic composition for preventing or ameliorating hyperemia containing a maple leaf extract.

In the present invention, the composition may be used for eye makeup products, and the eye makeup product may be any one selected from the group consisting of eyebrow pencils, eye liners, eye shadows, mascaras, and eye makeup removers.

As used herein, the term "maple", "hyperemia", and "prevention" are the same as explained above.

As used herein, the term "amelioration" refers to all of the actions by which the parameters associated with conditions under treatment (e.g., the symptoms) are at least lessened.

Still another aspect of the present invention provides a method for preventing or treating corneal diseases or conjunctival diseases including administering a pharmaceutical composition containing a maple leaf extract to the eyeball of a subject.

As used herein, the term "administration" is the same as explained above. With respect to the administration, in an exemplary embodiment of the present invention, a maple leaf extract was administered at concentrations of 0.1 mg/mL, 0.5 mg/mL, and 1.0 mg/mL in the morning and in the afternoon one day before the induction of hyperemia and in the morning on the same day that hyperemia was induced, but the administration is not limited thereto. Additionally, in another exemplary embodiment of the present invention, a maple leaf extract was administered at concentrations of 0.1 mg/mL, 0.5 mg/mL, and 1.0 mg/mL in the morning and in the afternoon for 7 days starting from the day when corneal damage was induced, but the administration is not limited thereto.

DETAILED DESCRIPTION OF THE INVENTION

Hereinafter, the present invention will be described in more detail with reference to the following Examples and Experimental Examples. However, these Examples and Experimental Examples are for illustrative purposes only and the invention is not limited by these Examples and Experimental Examples.

Example 1: Preparation of Maple Leaf Extract

Example 1-1: Preparation of Ethanol Extract (EE) of Maple Leaves

A pulverized product of maple leaves (1,700 g) was added into 25% ethanol (17 L) followed by sedimentation at room temperature. Then, the extract was concentrated under reduced pressure and lyophilized, and thereby a 25% ethanol extract of maple leaves in an amount of 78.57 g was obtained.

Example 1-2: Preparation of How-Water Extract (EW) of Maple Leaves

A pulverized product of maple leaves (1,700 g) was added into water (17 L) followed by sedimentation for 1 hour and subjected to hot-water extraction using the Gyeongseo Extractor (COSMOS 660, Incheon, Korea) for 3 hours. Then, the extract was lyophilized and a hot-water extract of maple leaves in an amount of 98.77 g was obtained.

The extracted maple leaf extract was filtered using a standard test sieve (150 μm, Retsch, Han, Germany) and concentrated in a lyophilizer until the extract became dry. The lyophilized maple leaf extract powder (50 mg) was dissolved in distilled water (1 mL), filtered through a disc filter (0.22 μm), and stored at −20° C. until use.

Experimental Example 1: Inhibitory Effect of Maple Leaf Extract Against Conjunctival Hyperemia in Rat Model Where Hyperemia was Induced by Capsaicin To confirm the inhibitory effect of a maple leaf extract against hyperemia, the degree of hyperemia was evaluated when hyperemia was induced using capsaicin after the maple leaf extract was administered to the eyeball of the rat. The specific details are described below.

Experimental Example 1-1: Preparation of Hyperemia-Inducing Material and Animal Model Thereof To induce hyperemia, capsaicin (Sigma, MO, USA) was dissolved in a solution containing 15% ethanol and 8.5% Tween-80, diluted with sterile physiological saline to a final concentration of 33 mM, and thereby a 1% capsaicin solution was prepared. The animal model in which hyperemia was induced was 6-week-old male SD rats purchased from Orientbio Inc. (Seongnam, Korea) and the rats were allowed to adapt for one week after purchase.

Experimental Example 1-2: Preparation of Maple Leaf Extracts with Various Concentrations and Administration Method Thereof Each of the extracts prepared in Example 1 was dissolved in sterile physiological saline according to the concentration suitable for the concentration of each group (low concentration group: 0.1 mg/mL, medium concentration group: 0.5 mg/mL, and high concentration group: 1.0 mg/mL). Each of the extracts according to the concentration was prepared on the same day that it was administered. Each of the extracts according to the concentration prepared daily was administered to the eye by instillation once in the morning and once in the afternoon in an amount of 20 μL before the administration of capsaicin, and further administered to the eye by instillation once in the morning on the same day when capsaicin was administered.

Experimental Example 1-3: Induction of Hyperemia Through Capsaicin and Evaluation Method of Hyperemia After the administration to the eye by instillation performed once in the morning in Experimental Example 1-2, the rats were subjected to general anesthesia by injecting pentobarbital sodium (30 mg/kg) into their abdominal cavities. Fifteen minutes after the administration to the eye by instillation, the capsaicin solution (20 μL) prepared in Example 1-1 was administered to the eye of the rats by instillation.

To evaluate the hyperemia degree of the conjunctival vessels, the eyes were opened and photographed using a stereoscopic microscope (Olympus, Tokyo, Japan). The images of the eyeballs were analyzed by photographing immediately before the administration of capsaicin, 30 minutes after the administration, and 1 hour after the administration.

Meanwhile, the hyperemia degree was evaluated according to the reported score evaluation method (*Clinical Ophthalmology* 2010; 4: 649 to 652) by assigning scores in the range of 0 to 4 as shown in Table 1.

TABLE 1

| Score | Evaluation Standard |
|---|---|
| 0 | Normal image of blood vessels of the limbus and external ocular muscle |
| 1 | General expansion of blood vessels of the limbus and external ocular muscle |
| 2 | Observation of new blood vessels by separation of blood vessels in the limbus |
| 3 | Observation of new blood vessels in the opened bulbar conjunctiva |
| 4 | Expansion of erythema in the opened bulbar conjunctiva |

Experimental Example 1-4: Results of Hyperemia Evaluation

As a result of the evaluation, in the case of a group where hyperemia was induced and neither the maple leaf ethanol extract (EE) nor the maple leaf hot-water extract (EW) was administered, new blood vessels appeared around the conjunctival area after capsaicin administration, compared to the blood vessels observed before capsaicin administration, and even in the case of the blood vessels observed before capsaicin administration, it was confirmed that they were expanded and became thicker after the administration. Additionally, with respect to the hyperemia score, most subjects were evaluated by 4 points and severe hyperemia was induced by capsaicin. However, in the group where EE and EW were administered to the eyeball by distillation, no new blood vessels were observed even after capsaicin administration (FIG. 1). Furthermore, in the case of the scores with respect to hyperemia evaluation, it was confirmed that as the administration concentrations of EE and EW became higher, the evaluation score became lower, and in particular, the group administered with EE showed a lower score compared to the group administered with EW (FIG. 2).

From the above results, it was confirmed that the maple leaf extract has an inhibitory effect against hyperemia and that the effect is dose-dependent. Furthermore, in light of the hyperemia evaluation score, it is thought that EE has a greater inhibitory effect against hyperemia compared to EW.

Experimental Example 2: Inhibitory Effect of Maple Leaf Extract Against Angiogenesis in Rats Where Corneal Damage was Induced by Alkali Burn To confirm the inhibitory effect of a maple leaf extract against angiogenesis, the rats in which corneal damage was induced by alkali burn were treated with a maple leaf extract and the degree of angiogenesis was evaluated. The specific details are described below.

Experimental Example 2-1: Induction of Corneal Damage in Rats by Alkali Burn and Administration of Maple Leaf Extract The 6-week-old male SD rats purchased from Orientbio Inc. (Seongnam, Korea) were allowed to adapt for one week as in Experimental Example 1-1. After one week, the rats were subjected to general anesthesia by injecting pentobarbital sodium (30 mg/kg) into their abdominal cavities. Then, in order to induce corneal damage, a filter paper was wetted with a 1 N sodium hydroxide (NaOH) solution (10 μL) and placed on top of the very central area of the cornea for 10 seconds. After 10 seconds, the filter paper was removed and the remaining NaOH solution was completely removed using sterile physiological saline (3 mL).

Then, the maple leaf extracts (EE, EW) prepared in the same manner as in Experimental Example 1-2 were administered to the eyeball by instillation once in the morning and once in the afternoon daily for 7 days.

Experimental Example 2-2: Evaluation of Degree of Corneal Angiogenesis

EE or EW of Experimental Example 2-1 was administered to the eyeball of each rat, and in the 7 days thereafter, each rat was subjected to general anesthesia by injecting pentobarbital sodium (30 mg/kg) into its abdominal cavity, and Evans blue dye dissolved in sterile PBS buffer was intravenously injected into each rat at a concentration of 45 mg/kg. After allowing Evans blue to diffuse into the systemic blood vessels for 10 minutes, the eyeball of each rat was ablated. After separating only the cornea from each rat, each cornea was placed on a slide under a microscope and the blood vessels newly formed on the corneal blood vessels were observed under a fluorescence microscope (BX51, Olympus, Tokyo, Japan).

As a result of the observation, blood vessels stained with Evans blue dye were not observed in the normal group where corneal damage was not induced, and thus the corneal area was shown to be dark, and also, the stained length of blood vessels was very short. That is, it was confirmed that there was almost no newly formed blood vessel. In contrast, blood vessels stained with Evans blue dye were observed in the groups where corneal damage was induced after one week of corneal damage and the stained length of blood vessels was long. That is, it was confirmed that blood vessels were elongated from the corneal area. However, as a result of administration of EE and EW to the eyeball by instillation for one week, it was confirmed that as the concentration of EE and EW became higher the blood vessels stained with Evans blue dye were reduced and thus the corneal area was observed to be dark, and also, the stained length of blood vessels was shown to be short in a concentration-dependent manner (FIGS. 3 and 4).

From the above results, it was confirmed that the maple leaf extracts have an inhibitory effect against corneal angiogenesis according to corneal damage on the eyeball and that the effect is concentration-dependent. Furthermore, in light of the length of the newly formed blood vessels, it is suggested that the inhibitory effect of EE against corneal angiogenesis is greater than that of EW.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:
1. A method for treating corneal diseases or conjunctival diseases, comprising a step of administering a pharmaceutically effective amount of a composition which comprises a maple leaf extract to the eyeball of a subject.

2. The method of claim 1, wherein the maple leaf extract is an ethanol extract of maple leaves.

3. The method of claim 1, wherein the maple leaf extract is a hot-water extract of maple leaves.

4. The method of claim 1, wherein the corneal disease is any one selected from the group consisting of hyperemia, corneal angiogenesis, dry eye syndrome and keratitis.

5. The method of claim 1, wherein the conjunctival disease is any one selected from the group consisting of conjunctivitis, pingueculitis, and pterygium.

6. The method of claim 1, wherein the composition is an external preparation for the eyeball.

7. The method of claim 1, wherein the composition further comprises a pharmaceutically acceptable carrier.

* * * * *